United States Patent
Manzke et al.

(10) Patent No.: US 9,533,173 B2
(45) Date of Patent: Jan. 3, 2017

(54) ADAPTIVE RADIOTHERAPY WITH SPECTRAL TISSUE OF INTEREST IMAGING AND TRACKING

(71) Applicant: KONINKLIJKE PHILIPS N.V., Eindhoven (NL)

(72) Inventors: Robert Manzke, Bonebuttel (DE); Carsten Oliver Schirra, St. Louis, MO (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 104 days.

(21) Appl. No.: 14/377,190

(22) PCT Filed: Feb. 7, 2013

(86) PCT No.: PCT/IB2013/050994
§ 371 (c)(1),
(2) Date: Aug. 7, 2014

(87) PCT Pub. No.: WO2013/124754
PCT Pub. Date: Aug. 29, 2013

(65) Prior Publication Data
US 2016/0016009 A1    Jan. 21, 2016

Related U.S. Application Data

(60) Provisional application No. 61/601,088, filed on Feb. 21, 2012.

(51) Int. Cl.
G06K 9/00 (2006.01)
A61N 5/10 (2006.01)
(Continued)

(52) U.S. Cl.
CPC ........... *A61N 5/1065* (2013.01); *A61B 6/4241* (2013.01); *A61B 6/481* (2013.01); *A61B 6/482* (2013.01);
(Continued)

(58) Field of Classification Search
USPC ................................................. 382/128–134
See application file for complete search history.

(56) References Cited

U.S. PATENT DOCUMENTS 8,050,348 B2    11/2011 Kim et al.
2005/0059887 A1    3/2005 Mostafavi et al.
(Continued)

FOREIGN PATENT DOCUMENTS

WO    2006130659 A2    12/2006

OTHER PUBLICATIONS

Berbeco, R., et al.; Localized dose enhancement to tumor blood vessel endothelial cells via megavoltage X-rays and targeted gold nanoparticles: new potential for external beam radiotherapy; 2011; Int. J. Radiat. Oncol. Biol. Phys.; 81 (1)270-276.
(Continued)

*Primary Examiner* — Alex Liew (57) ABSTRACT

A radio therapy apparatus (100) includes a tissue of interest tracker (124) that receives a first image of tissue of interest and a second later acquired spectral image of the tissue of interest and tracks a change in a geometry and/or location of the tissue of interest based at least on the first and second images and generates a signal indicative of the change. The second image is generated based on a first spectral signal corresponding to an output of an energy-resolving radiation sensitive detector array for a first predetermined energy range and a second spectral signal corresponding to an output of the energy-resolving radiation sensitive detector array for a second predetermined energy range and visually
(Continued)

enhances scanned structure corresponding to the first or second signals while visually suppressing scanned structure corresponding to the other of the first or second signals. An adaptive planner (126) updates a radiotherapy treatment plan based on the signal.

15 Claims, 4 Drawing Sheets

(51) Int. Cl.
*A61B 6/00* (2006.01)
*G06T 7/00* (2006.01)

(52) U.S. Cl.
CPC ............ *A61B 34/20* (2016.02); *A61N 5/1064* (2013.01); *G06T 7/0012* (2013.01); *G06T 7/0044* (2013.01); *A61B 6/4266* (2013.01); *A61B 34/10* (2016.02); *A61B 2034/2065* (2016.02); *A61B 2090/376* (2016.02); *A61B 2090/3966* (2016.02); *A61N 2005/1061* (2013.01); *G06T 2207/10128* (2013.01); *G06T 2207/30024* (2013.01)

(56) References Cited

U.S. PATENT DOCUMENTS

| 2006/0109951 | A1* | 5/2006 | Popescu | A61B 6/032 378/4 |
| 2008/0063135 | A1* | 3/2008 | DeMan | A61B 6/032 378/4 |
| 2010/0054576 | A1* | 3/2010 | Tsujita | G06K 9/2018 382/134 |
| 2010/0316259 | A1 | 12/2010 | Liu et al. | |
| 2012/0039519 | A1 | 2/2012 | Fei et al. | |

OTHER PUBLICATIONS

Cormode, D. P., et al.; Atherosclerotic Plaque Composition: Analysis with Multicolor CT and Targeted Gold Nanoparticles; 2010; Radiology; 256(3)774-782.

Hainfeld, J.F., et al.; Radiotherapy enhancement with gold nanoparticles; 2008; J. Pharm. Pharmacol.; 60(8) 977-985.

Keall, P. J., et al.; The management of respiratory motion in radiation oncology report of AAPM Task Group 76a; 2006; Med. Phys.; 33(10)3874-3900.

Mackie, T. R., et al.; Tomotherapy: A new concept for the delivery of dynamic conformal radiotherapy; 1993; Med. Phys.; 20(6)1709-1719.

Pan, D., et al.; Computed Tomography in Color: NanoK-Enhanced Spectral CT Molecular Imaging; 2010; Angew Chem Int Ed Engl; 49(50)9635-9639.

Popovtzer, R., et al.; Targeted Gold Nanoparticles enable Molecular CT Imaging of Cancer; 2008; Nano Lett.; 8(12) 4593-4596.

Wiersma, R. D., et al.; Combined kV and MV Imaging for real-time tracking of implanted fiducial markers; 2008; Med. Phys.; 35(4)1191-1198.

\* cited by examiner

ADAPTIVE RADIOTHERAPY WITH SPECTRAL TISSUE OF INTEREST IMAGING AND TRACKING

CROSS REFERENCE TO RELATED APPLICATIONS

This application is a national filing of PCT application Serial No. PCT/IB2013/050994, filed Feb. 7, 2013, published as WO 2013/124754 A1 on Aug. 29, 2013, which claims the benefit of U.S. provisional application Ser. No. 61/601,088 filed Feb. 21, 2012, which is incorporated herein by reference.

The following generally relates adaptive radiotherapy and more particularly to an adaptive radiotherapy with spectral tissue of interest imaging and tracking.

Radiotherapy (also referred to as radiation oncology and radiation therapy) is a technique in which ionizing radiation is used to control or kill tissue of interest, such as tumor cells, and works by damaging the DNA of the cells of the tissue of interest. With radiotherapy, the patient typically receives a dose of ionizing radiation administered regularly (e.g. daily) over a period of time, for example, on the order of several weeks. During a treatment session, the patient is positioned in an examination region of a radiotherapy device (generally referred to as a linear accelerator or a linac), which is used to irradiate the tumor. To spare surrounding tissue, the radiotherapy plan typically defines a beam shape and several angles of exposure that intersect at the tissue of interest, which results in an absorbed dose that is localized to the tissue of interest. A margin of tissue around the tissue of interest can been defined to allow for uncertainty in the treatment plan.

Over the course of the treatment sessions, a geometry (e.g., size and/or shape) of the tissue of interest and/or a location of the tissue of interest in the patient may change within the patient. This can occur due to shrinkage of the tissue of interest, patient weight loss, internal organ movement (e.g., respiration), etc. As a consequence, the radiotherapy plan may no longer optimize treatment of the tissue of interest or mitigate damage to surrounding tissue. This has been compensated for through tumor tracking and adaptive radiotherapy planning in which the relative geometry and/or location changes of the tissue of interest in the patient after the radiotherapy plan is created and before a treatment or subsequent treatment is tracked and used to update the radiotherapy plan for a treatment session. Such tracking has be achieved using bi-planar or CT-based kilovolt (kV) and/or megavolt (MV) imaging of gold beads implanted in or close proximity to the tissue of interest.

For tissue of interest tracking, the patient is scanned and the relative geometry and the location of the tissue of interest is determined with respect to the gold beads in the resulting images. The radiotherapy plan can then be updated based on this information and the initial plan so that the treatment beam again is substantially localized only at the tissue of interest. Examples of such tracking are discussed in T. R. Mackie et al., "Tomotherapy: a new concept for the delivery of dynamic conformal radiotherapy," *MEDICAL PHYSICS-LANCASTER PA*, vol. 20, pp. 1709-1709, 1993, P. J. Keall et al., "The management of respiratory motion in radiation oncology report of AAPM Task Group 76," *Medical physics*, vol. 33, p. 3874, 2006, and R. D. Wiersma, W. Mao, and L. Xing, "Combined kV and MV imaging for real-time tracking of implanted fiducial markers," *Medical Physics*, vol. 35, no. 4, p. 1191, 2008.

Unfortunately, implanting such beads in or close to the tissue of interest in the patient is an invasive procedure and can be a challenging task. In view of at least the above, there is an unresolved need for one or more other approaches to tissue of interest tracking and updating a radiotherapy plan based thereon in adaptive radiotherapy.

Aspects described herein address the above-referenced problems and others.

In one aspect, a radiotherapy apparatus includes a tissue of interest tracker that receives a first image of tissue of interest and a second later acquired spectral image of the tissue of interest and tracks a change in a geometry and/or location of the tissue of interest based at least on the first and second images and generates a signal indicative of the change. The second later acquired spectral image is generated based on a first spectral signal corresponding to an output of an energy-resolving radiation sensitive detector array for a first predetermined energy range and a second spectral signal corresponding to an output of the energy-resolving radiation sensitive detector array for a second predetermined energy range. The second later acquired spectral image visually enhances scanned structure corresponding to the first or second signals while visually suppressing scanned structure corresponding to the other of the first or second signals. An adaptive planner updates a radiotherapy treatment plan based on the signal indicative of the change from the tissue of interest tracker.

In another aspect, an imaging method for a radiotherapy system includes receiving imaging data from an energy-resolving radiation sensitive detector array of the radiotherapy system, obtaining a predetermined sub-energy range of interest, which is a sub-energy range of the acquired data energy range, selecting sub-imaging of the received imaging data corresponding to the obtained sub-energy range of interest, and generating a spectral image based on the selected sub-imaging data.

In another aspect, a method includes obtaining a first image of tissue of interest, obtaining a second image of the tissue of interest, including a spectral composition of the tissue of interest, determining a changes in the tissue of interest between the first and second images, and updating a therapy plan based on the determined change to the tissue of interest.

The invention may take form in various components and arrangements of components, and in various steps and arrangements of steps. The drawings are only for purposes of illustrating the preferred embodiments and are not to be construed as limiting the invention.

The following describes an adaptive radiotherapy approach in which spectral x-ray and/or spectral CT imaging capabilities of a radiotherapy apparatus are configured to image gold and/or other k-edge material doped nanoparticles (which are targeted to tissue of interest in a patient and optionally used enhance local dose to the cells of the tissue of interest during a radiotherapy session of the patient) to produce contrast enhanced spectral images of the tissue of interest. This may improve the contrast enhancement of the tissue of interest, relative to a configuration in which such spectral imaging capabilities are not present, which allows for improved tissue of interest tracking and targeting in adaptive radiotherapy without interventional marker bead implantation in the patient.

Figure 1:
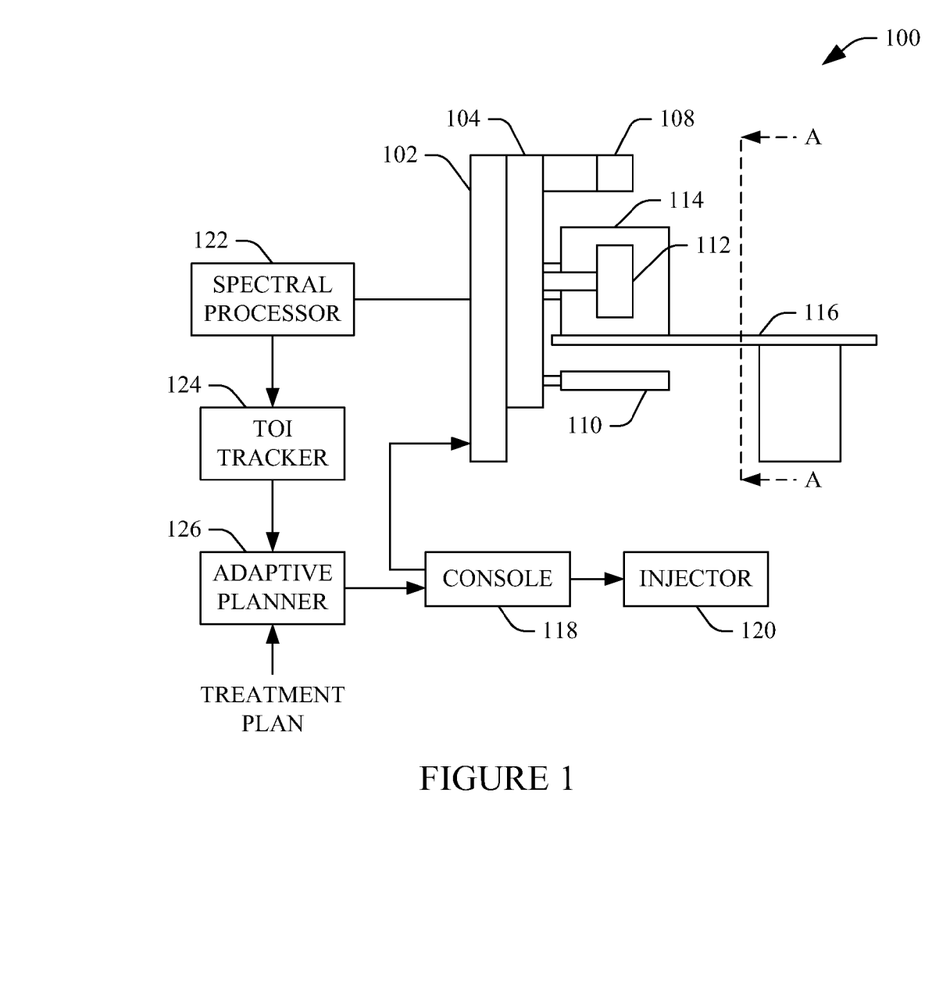
FIG. 1 schematically illustrates a side view of an example radiotherapy system that includes energy-resolving radiation sensitive detectors.
Figure 2:
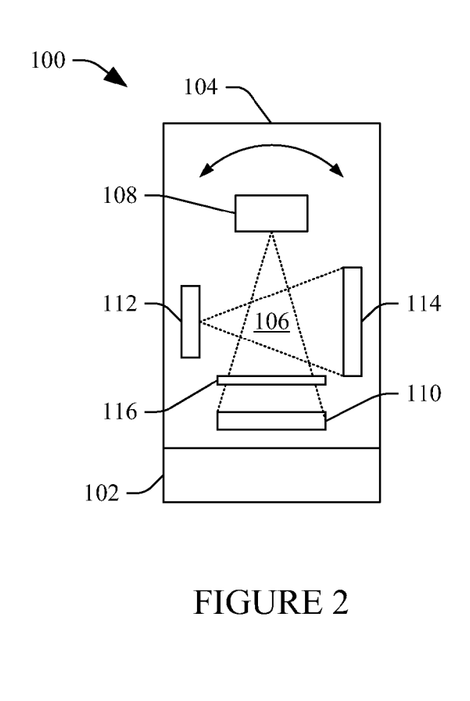
FIG. 2 schematically illustrates a front view looking into the example radiotherapy system of FIG. 1 along line A-A.

FIGS. 1 and 2 schematically illustrate an example radiotherapy apparatus 100 that includes spectral imaging hardware and capabilities. FIG. 1 schematically illustrates a side view of the example radiotherapy apparatus 100, and FIG. 2 schematically illustrates a front view looking into the example radiotherapy apparatus 100 along line A-A of FIG. 1.

The illustrated radiotherapy apparatus 100 includes a generally stationary portion 102 and a rotatable portion 104, which is rotatably supported by the generally stationary portion 102 and rotates about an examination region 106. The rotatable portion 104 is configured to rotate over a predetermined angular range or arc, such as two hundred degrees, or more or less than two hundred degrees.

The radiotherapy apparatus 100 further includes a radiation source 108, such as a megavolt (MV) radiation source, which is supported by and rotates with the rotatable portion 104. In this example, the radiation source 108 is configured at least as a radiotherapy treatment source for radiotherapy apparatus 100. Optionally, the radiation source 108, in connection with an optional two-dimensional (e.g., a flap panel) detector array 110, is also configured as an imaging source. The radiation source 108, as shown, is located opposite the detector array 110, across the examination region 106. The source 108 and the detector array 110 form a source/detector pair 108/110.

The illustrated radiotherapy apparatus 100 also includes a radiation source 112, such as a kilovolt (kV) source. Likewise, the radiation source 112 is supported by and rotates with the rotatable portion 104 about the examination region 106. In this example, the source 112, in connection with a two-dimensional (e.g., a flat panel) detector array 114, is configured as an imaging source. Likewise, the radiation source 112, as shown, is located opposite the detector array 114, across the examination region 106. The source 112 and the detector array 114 form a source/detector pair 112/114.

In the illustrated embodiment, the source/detector pair 108/110 and the source/detector pair 112/114 are angularly offset from each other by approximately ninety degrees, as shown in FIG. 2. However, in other embodiments, the angularly offset may be different. Furthermore, the illustrated source/detector pair 112/114 includes an x-ray source/detector pair. However, in another embodiment, the source/detector pair 112/114 alternatively or additionally includes a cone beam computed tomography (CT) source/detector pair.

Generally, for radiotherapy treatment, the source 108 emits a treatment beam, which is directed at and irradiates tissue of interest (e.g., a tumor or other tissue of interest) of a patient on a subject support 116, which is used to position the patient in the examination region 106 for treatment and/or imaging. The source 108 can be rotated to one or more predetermined angular locations and/or the subject support 116 can be moved to facilitate directing the treatment beam according to the radiotherapy plan and/or user changes thereto.

For imaging with the source 108/detector pair 110, the source 108 emits radiation, while at one or more static positions or while moving along the arc, that traverses the patient in the examination region 106, and the detector array 110 detects the radiation that traverses the patient in the examination region 106 and generates an image indicative thereof. At a static position, the image is a two dimensional projection image. Projection images acquired at different angular positions can be used to produce a three dimensional image.

It is to be appreciated that treatment and imaging using the source 108 can be performed serially or concurrently.

For imaging with the source/detector pair 112/114, the source 112 emits radiation, while at one or more static positions or while moving along the arc, that traverses the patient in the examination region 106, and the detector array 114 detects the radiation that traverses the patient in the examination region 106 and generates an image indicative thereof. At a static position, the image is a two dimensional projection image. Projection images acquired at different angular positions can be used to produce a three dimensional image.

Figure 3:
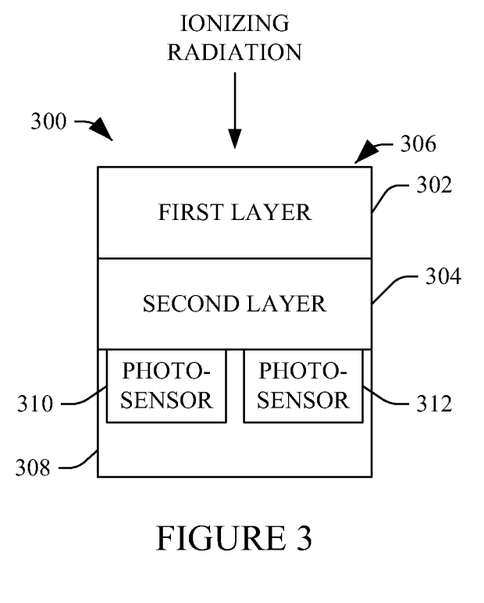
FIG. 3 schematically illustrates an example scintillator/back mounted photosensor energy-resolving radiation sensitive detector.
Figure 4:
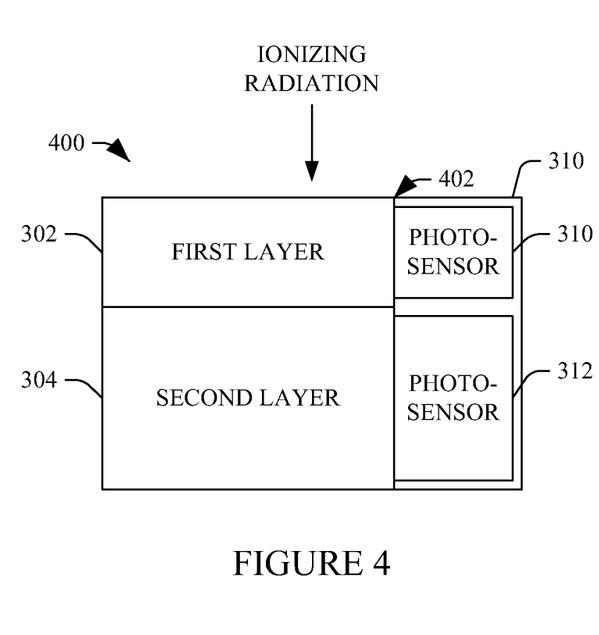
FIG. 4 schematically illustrates an example scintillator/side mounted photosensor energy-resolving radiation sensitive detector.

In the illustrated embodiment, at least one of the detectors 110 or 114 includes energy-resolving detector pixels, including scintillator-based multi-spectral detectors and/or direct conversion detector pixels (e.g., Si, Ge, GaAs, CdTe, CdZnTe, etc.). FIGS. 3 and 4 respectively illustrate non-limiting examples of scintillator-based multi-spectral detectors and FIGS. 5 and 6 illustrate a non-limiting example of direction conversion detector photon counting circuitry.

Turning briefly to FIG. 3, the energy-resolving detector 300 includes a first layer 302 of scintillation material and a second layer 304 of scintillation material. The first and second layers 302 and 304 are coupled such that the first layer 302 is on a side 306 of the detector receiving incoming radiation. A photosensor 308 is coupled to a second opposing side of the detector 300 and includes photodiodes 310 and 312 facing the layers 302 and 304. Energy absorption, generally, is dependent on the thickness thereof. As such, in this example, lower energy photons are absorbed in the first layer 302 and higher energy photons are absorbed in the second layer 304.

The photodiodes 310 and 312 respectively have emission spectra that match the spectral sensitivities of the layers 302 and 304. As such, only the light emitted by the first layer 302 is absorbed by the photodiode 310, and only the light emitted by the second layer 304 is absorbed by the photodiode 312, and the photodiodes 310 and 311 respectively output signals indicative of radiation from different energy bands, which correspond to the first and second layers 302 and 304. FIG. 4 shows a detector 400 in which the photosensor array 310 is coupled to a side 402 of the scintillator layers, which is perpendicular to the direction of incoming radiation. Other variations may include more scintillation layers/photosensors, and individual scintillation layers may have equal thickness (e.g., FIG. 3) and/or different thickness (e.g., FIG. 4).

Figure 5:
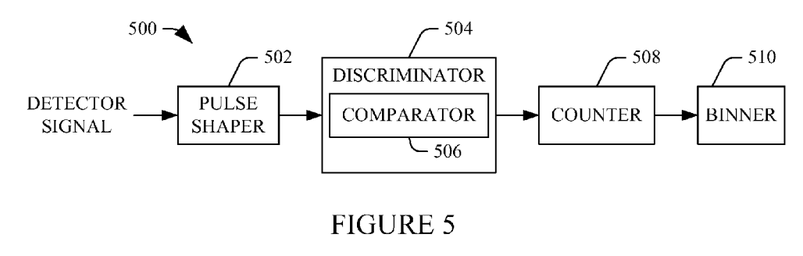
FIG. 5 schematically illustrates direct conversion energy-resolving circuitry for a direct conversion detector of the example radiotherapy system of FIG. 1.
Figure 6:
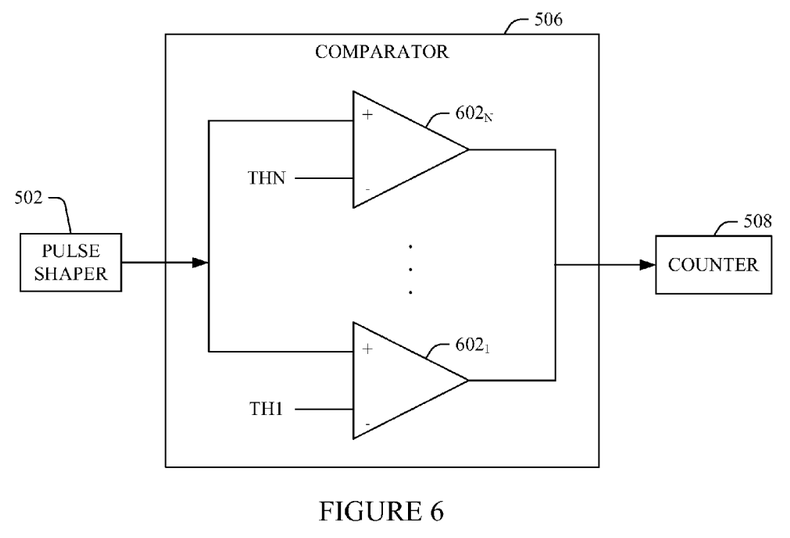
FIG. 6 schematically illustrates an example comparator of the discriminator of the energy-resolving circuitry of FIG. 5.

FIGS. 5 and 6 schematically illustrate non-limiting circuitry 500 for processing an output signal of a direct conversion energy-resolving detector (and/or a conventional integrating scintillator/photosensor detector). Generally, the output of such a detector includes an electrical current or voltage signals having a peak amplitude that is indicative of the energy of a detected photon. A pulse shaper 502 processes the signal and generates a pulse such as voltage or other pulse indicative of the energy of the detected photon. It is to be appreciated that the detector signal may be amplified and/or otherwise processed before being processed by the pulse shaper 702.

An energy-discriminator 504 energy discriminates the pulse. In the illustrated example, the energy-discriminator 504 includes a comparator 506 that compares the amplitude of the pulse with two or more different energy thresholds, which correspond to different energies of interest. The comparator 506 produces an output signal indicative of the energy of the photon based on the comparison. This is shown in FIG. 6, where the comparator 506 includes N sub-comparators $602_1, \ldots, 602_N$, wherein N is an integer. Each of the sub-comparators $606_1, \ldots, 606_N$ includes a first input, which receives the output of the pulse shaper 502 and a second input, which receives a threshold value $TH_1, \ldots, TH_N$, and the comparator 506 produces an output signal indicative of whether the amplitude of the incoming pulse exceeds the corresponding thresholds.

Returning to FIG. 5, a counter 508 increments a count value for each threshold based on the output of the energy discriminator 506. For instance, when the output of the comparator 506 for a particular threshold indicates that the amplitude of the pulse exceeds the corresponding threshold, the count value for that threshold is incremented. A binner 510 energy bins the signals and, hence, the photons into two or more energy bins based on the counts. An energy bin generally encompass an energy sub-range or window. For example, a bin may be defined for the energy range between two thresholds, where a photon resulting in a count for the lower threshold but not for higher threshold would be assigned to that bin.

Returning to FIGS. 1 and 2, a general purpose computer serves as an operator console 118. The console 118 includes a human readable output device such as a monitor or display and an input device such as a keyboard and mouse. Software resident on the console 118 allows the operator to interact with the scanner 100 via a graphical user interface (GUI) or otherwise. A processor of the console 118 executes the software, which is stored in computer readable storage medium, such as physical memory, of the console 118. Additionally or alternatively, some or all of the software can be stored on transitory medium such a carrier wave or signal.

An injector 120 is configured to inject a contrast material(s), for example, for a contrast enhanced imaging procedure. The illustrated injector 120 is controlled by the console 118. However, in an alternative embodiment, the contrast agent is manually administered, and the injector 120 can be omitted. A suitable contrast material includes target specific (e.g., a tumor) nanoparticles doped with gold, bismuth, gadolinium, etc. and/or other k-edge material. Nanoparticles doped with gold or other suitable material and targeted to specific cancer cells using dedicated antigens is discussed in R. Popovtzer et al., "Targeted Gold Nanoparticles enable Molecular CT Imaging of Cancer," *Nano letters*, vol. 8, no. 12, pp. 4593-4596, December 2008.

Contrast materials with gold or other k-edge materials are discussed in D. P. Cormode et al., "Atherosclerotic Plaque Composition: Analysis with Multicolor CT and Targeted Gold Nanoparticles 1," *Radiology*, vol. 256, no. 3, pp. 774-782, 2010 and Pan, D. (2010). Computed Tomography in Color: NanoK-Enhanced Spectral CT Molecular imaging. *Angewandte Chemie*, 9635-9. Using such a contrast material along with the energy-resolving detectors (detectors 110 and/or 114) allows for tissue of interest tracking without implanted beads as the acquired data can be spectrally separated based on energy and images of the gold nanoparticles and, hence, substantially only the tissue of interest can be generated.

Moreover, gold doped nanoparticles may also allow for enhancing localized dose to the treated tumor, which may improve the efficacy of the radiotherapy treatment. Utilizing nanoparticles as such is discussed in R. I. Berbeco, W. Ngwa, and G. M. Makrigiorgos, "Localized Dose Enhancement to Tumor Blood Vessel Endothelial Cells via Megavoltage X-rays and Targeted Gold Nanoparticles: New Potential for External Beam Radiotherapy," *International Journal of Radiation Oncology*Biology*Physics*, vol. 81, no. 1, pp. 270-276, September 2011, and J. F. Hainfeld, F. A. Dilmanian, D. N. Slatkin, and H. M. Smilowitz, "Radiotherapy enhancement with gold nanoparticles," *Journal of Pharmacy and Pharmacology*, vol. 60, no. 8, pp. 977-985, 2008.

A spectral processor 122 processes the signals from the energy-resolving detectors 110 and/or 114. The spectral processor 122 can generate an image with data corresponding to one of the different energy ranges or two or more (including all) of the different energy ranges. For example, where one energy range corresponds to a k-edge of a k-edge material dope to a nanoparticle attached to the tissue of interest, the spectral processor 122 can process only the data corresponding to the radiation having energy in the energy range of the k-edge material, thereby producing a spectral image in which the tissue of interest is visually enhanced and other tissue is visually suppressed.

A tissue of interest (TOI) tracker 124 receives the spectral image of the tissue of interest (and/or other image) from the spectral processor 122 and tracks the geometry and/or location of the tissue of interest in the subject based at least on the spectral image of the tissue of interest and a previously acquired image. For example, the TOI tracker 124 may superimpose, combine, register, etc. the spectral image of the tissue of interest with the previous image, such as the initial planning image, an image after one or more treatments, an image before positioning the subject in the examination region 106, etc. The TOI tracker 124 visually presents the resulting data in a graphical user interface (GUI).

The TOI tracker 124 can, automatically without user interaction or with user interaction, determine any change in geometry and/or location of the tissue of interest. The TOI tracker 124 can generate a signal indicative of any change. The signal may include numerical values, a visual representation (e.g., displayed in the GUI), and/or other information. This can be performed for real-time and/or inter-fractional tracking. Known and/or other automatic and/or user interaction based segmentation approaches can be used to identify the geometry and/or location in the images, and known and/or other automatic and/or user interaction based measurement tools can be used to measure any change in geometry and/or location.

An adaptive planner 126 updates, automatically and/or with user interaction, the treatment plan based on the signal from the TIO tracker 124. The update may include updating the position of the treatment source 108 and/or the subject support 116 to re-focus the treatment beam so that the treatment beam once again is substantially localized only at the tissue of interest. With user interaction updates, the adaptive planner 126 visually presents a proposed recommended update via a GUI, and the user accepts, modifies or rejects the update.

The updated plan is provided to the console 118, which uses the plan to position the treatment source 108 and/or the subject support 116. Alternatively, the user uses the update plan to position the treatment source 108 and/or the subject support 116. The treatment plan can be created based on images acquired by the system 100 and/or other system such as a CT scanner, a magnetic resonance (MR) scanner, positron emission tomography (PET), etc.

Variations are contemplated.

In the illustrated embodiment, the radiotherapy apparatus 100 includes a single x-ray or CT source 112. In another embodiment, the radiotherapy apparatus 100 includes two or more sources 112 and corresponding detectors 114, arranged at different angular locations with respect to each other in the x/y plane, where at least two of the radiation sources 112 emit radiation with different energy spectra. The at least two of the two or more radiation sources can be concurrently or individually employed during a same scan and different scans.

Additionally or alternatively, at least one of the sources 110 or 112 is configured to switch between two or more emission voltages, for example, the source 112 can be configure to switch between 20 kVp to 140 kVp and/or other combination of kVps. A source controller or the like can switch the radiation source voltage from scan to scan, integration period to integration period, within an integration period, and/or otherwise. As a result, radiation beams having different mean emission energy spectra can be generated.

In another embodiment, one or more of the detector 110 or the source/detector pair 112/114 are omitted from the radiotherapy apparatus 110. Where either or both are omitted, a spectral imaging scanner separate from the radiotherapy apparatus 100 can be used for spectral imaging.

Figure 7:
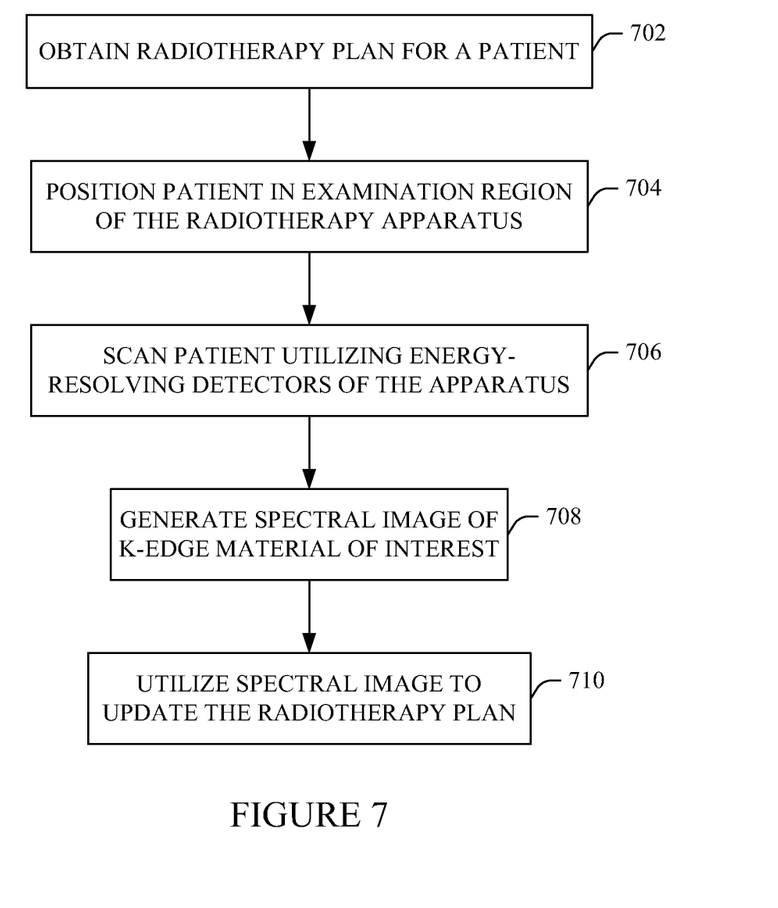
FIG. 7 illustrates an example method.

FIG. 7 illustrate an example method.

It is to be appreciated that the ordering of the acts in the methods described herein is not limiting. As such, other orderings are contemplated herein. In addition, one or more acts may be omitted and/or one or more additional acts may be included.

At 702, a radiotherapy plan is obtained for a patient. This plan can be created using known and/or other approaches.

At 704, a patient is positioned in the examination region 106 of the radiotherapy apparatus 100.

At 706, the patient is scanned using at least one of the source/detector pairs 108/110 or 112/114.

At 708, the acquired data is processed to produce a spectral image of a k-edge material of a nanoparticle attached to tissue of interest of the patient, wherein the spectral image visually enhances the k-edge material in the spectral image while visually suppressing other material in the spectral image.

At 710, the spectral image is used to update the radiotherapy plan, including updating parameters that are based on the geometry and/or location of the tissue of interest in the patient, as described herein.

For example, the spectral image can be compared with a previously acquired image, and a geometry and/or location change in the tissue of interest, as determined between the two images, can be used to update the therapy plan.

It is to be appreciated that the updated radiotherapy plan can be used when employing the radiotherapy apparatus 100 to treat the tissue of interest. Furthermore, the nanoparticles may facilitate localizing dose enhancement to the tissue of interest during treatment of the tissue of interest using the radiotherapy apparatus 100.

At least a portion of the above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A radiotherapy apparatus, comprising:
    a tissue of interest tracker that receives a first image of tissue of interest and a second later acquired spectral image of the tissue of interest and tracks a change in a geometry and/or location of the tissue of interest based at least on the first and second images and generates a signal indicative of the change,
    wherein the second later acquired spectral image is generated based on a first spectral signal corresponding to an output of an energy-resolving radiation sensitive detector array of the radiotherapy apparatus for a first predetermined energy range and a second spectral signal corresponding to an output of the energy-resolving radiation sensitive detector array of the radiotherapy apparatus for a second predetermined energy range,
    wherein the second later acquired spectral image visually enhances scanned structure corresponding to the first or second signals while visually suppressing scanned structure corresponding to the other of the first or second signals; and
    an adaptive planner that updates a radiotherapy treatment plan based on the signal indicative of the change from the tissue of interest tracker.

2. The radiotherapy apparatus of claim 1, wherein the tissue of interest tracker visually presents a superposition of the first and the second images, including indicia corresponding to the change in the geometry and/or the location of the tissue of interest.

3. The radiotherapy apparatus of claim 1, wherein adaptive planner visually presents a recommended update and updates the radiotherapy treatment plan with the update in response to receiving a signal indicative of user confirmation of the update.

4. The radiotherapy apparatus of claim 1, wherein the update includes updating at least one of a position of a treatment source or a position of a subject support to re-focus a treatment beam so that the treatment beam is substantially localized only at the tissue of interest.

5. The radiotherapy apparatus of claim 1, further comprising:
    at least one radiation source that emits ionizing radiation that traverses an examination region; and
    at least one energy-resolving radiation sensitive detector array that detects ionizing radiation that traverses the examination region and generates the first and second spectral signals.

6. The radiotherapy apparatus of claim 5, wherein the at least one radiation source is a megavolt source.

7. The radiotherapy apparatus of claim 5, wherein the at least one radiation source is a kilovolt source.

8. The radiotherapy apparatus of claim 5, wherein the at least one radiation source includes a megavolt radiation source and a kilovolt radiation source.

9. The radiotherapy apparatus of claim 5, wherein the detector array includes at least one scintillator/photodiode pair based detector having a spectral sensitivity corresponding only to the first or second energy range.

10. The radiotherapy apparatus of claim 5, wherein the detector array includes at least one direct conversion photon counting detector and corresponding energy resolving circuitry.

11. The radiotherapy apparatus of claim 1, wherein at least one of the first or second energy ranges corresponds to a k-edge energy of interest.

12. The radiotherapy apparatus of claim 11, wherein the k-edge energy of interest corresponds to a k-edge energy of nanoparticles bound to tissue of interest of a patient.

13. The radiotherapy apparatus of claim 1, further comprising:
a console that controls an injector administering the contrast material.

14. The radiotherapy apparatus of claim 1, further comprising:
a treatment source, wherein the spectral image is used to determine at least one operating parameter of the treatment source.

15. A non-transitory computer readable medium encoded with computer readable instructions which when executed by a computer processor causes the computer processor to:
receive a first image of tissue of interest and a second later acquired spectral image of the tissue of interest,
wherein the second later acquired spectral image is generated based on a first spectral signal corresponding to an output of an energy-resolving radiation sensitive detector array of the radiotherapy apparatus for a first predetermined energy range and a second spectral signal corresponding to an output of the energy-resolving radiation sensitive detector array of the radiotherapy apparatus for a second predetermined energy range, and the second later acquired spectral image visually enhances scanned structure corresponding to the first or second signals while visually suppressing scanned structure corresponding to the other of the first or second signals;
track a change in a geometry and/or location of the tissue of interest based at least on the first and second images and generates a signal indicative of the change; and
update a radiotherapy treatment plan based on the signal indicative of the change from the tissue of interest tracker.

* * * * *